United States Patent
Tropsch et al.

(10) Patent No.: US 6,458,348 B1
(45) Date of Patent: *Oct. 1, 2002

(54) USE OF WATER-SOLUBLE POLYMERS AS BIOCIDES

(75) Inventors: Jürgen Tropsch, Römerberg; Dieter Zeller, Wiesloch; Anton Negele, Deidesheim; Norbert Mahr, Limburgerhof; Jürgen Decker, Trier, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/508,001

(22) PCT Filed: Sep. 8, 1997

(86) PCT No.: PCT/EP98/05625

§ 371 (c)(1),
(2), (4) Date: Mar. 7, 2000

(87) PCT Pub. No.: WO99/12420

PCT Pub. Date: Mar. 18, 1999

(30) Foreign Application Priority Data

Sep. 8, 1997 (DE) .......................... 197 39 304

(51) Int. Cl.$^7$ .......................... A01N 37/18; A01N 37/36
(52) U.S. Cl. ................. 424/78.35; 523/122; 525/328.2; 525/328.4; 525/384; 525/386; 526/304
(58) Field of Search ............................ 525/328.2, 328.4, 525/384, 386; 523/122; 424/78.35; 526/304

(56) References Cited

U.S. PATENT DOCUMENTS 6,261,581 B1 * 7/2001 Gebhardt et al. ......... 424/78.35
6,271,327 B1 * 8/2001 Niessner et al. ............ 526/304

* cited by examiner

Primary Examiner—D. R. Wilson
(74) Attorney, Agent, or Firm—Keil & Weinkauf

(57) ABSTRACT

The use of polymers comprising as essential structural elements units of the formula I and/or II

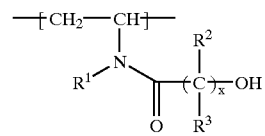

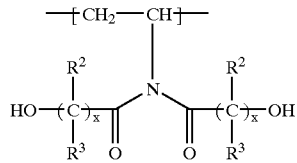

in which $R^1$ is H, alkyl, cycloalkyl, aryl or aralkyl, $R^2$ and $R^3$ independently of one another are defined as for $R^1$ or are selected from substituted alkyl, substituted cycloalkyl, substituted aryl or substituted aralkyl, the substituents being selected from OH, O-alkyl, O-aryl, SH, S-alkyl, S-aryl, $NH_2$, NH-alkyl, NH-aryl, N(alkyl)$_2$, in protonated form if desired, N(alkyl)$_3{}^+Z^{31}$, where Z is the radical of an organic or inorganic acid, COOH, COO-alkyl, $CONH_2$, CONH-alkyl, CON(alkyl)$_2$, CN and $SO_3H$; and the indices x in each case independently of one another are an integer from 1 to 20, and their corresponding acid addition salts as biocides.

4 Claims, No Drawings

USE OF WATER-SOLUBLE POLYMERS AS BIOCIDES

The invention relates to the use of polymers comprising as essential structural elements units of the formula I and/or II

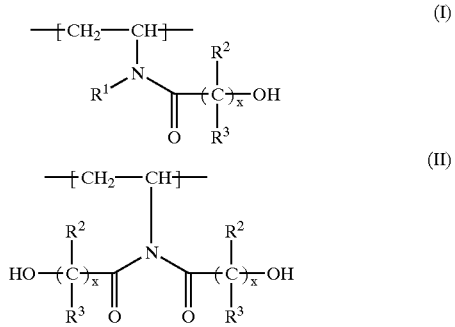

in which

R$^1$ is H, alkyl, cycloalkyl, aryl or aralkyl,

R$^2$ and R$^3$ independently of one another are defined as for R$^1$ or are selected from substituted alkyl, substituted cycloalkyl, substituted aryl or substituted aralkyl, the substituents being selected from OH, O-alkyl, O-aryl, SH, S-alkyl, S-aryl, NH$_2$, NH-alkyl, NH-aryl, N(alkyl)$_2$, in protonated form if desired, N(alkyl)$_3$$^+$Z$^-$, where Z is the radical of an organic or inorganic acid, COOH, COO-alkyl, CONH$_2$, CONH-alkyl, CON(alkyl)$_2$, CN and SO$_3$H; and the indices x in each case independently of one another are an integer from 1 to 20, and their corresponding acid addition salts as biocides.

Z. Chem. 27 (1987) 1 discloses specially functionalized polyvinyl alcohols, polyacrylates and polyethyleneimines for immobilizing antimicrobially active substances. In the course of the use of such systems, the active substances are released in a controlled manner. According to the information in the publication, however, the antimicrobial activity is based on the release of the biocidal active substances.

U.S. Pat. No. 1,071,630 discloses that copolymers of diallyldimethylammonium chloride and sodium acrylate have a bactericidal activity. EP-A 0 331 528 discloses copolymers of ethylene and dialkylaminoalkylacrylamides having biocidal activity.

Antimicrobially active polymers containing vinylphosphonium and vinylsulfonium groups were reported in J. Polym. Sci. part A: Polym. Chem., Vol. 31, 335, 1441, 1467 and 2873 and also in Arch. Pharm. (Weinheim) 321 (1988) 89. Biocidally active polymers containing vinylamine units are known from Makromol. Chemie.

U.S. Pat. No. 4,493,193 describes N-containing polymers as biocides. However, the nitrogen atoms are situated in the main chain of the polymer. Similar polymer structures are also described in U.S. Pat. No. 3,714,259.

It is an object of the present invention to provide novel biocidal compositions.

We have found that this object is achieved in accordance with the invention by the use as biocides of the polymers defined at the outset.

The polymers to be used in accordance with the invention are known from the earlier application P1 96/30977.8. Essential structural elements present in these polymers are hydroxy-substituted N-vinylcarboxamide units.

Unless specified otherwise, the specific description given below of the polymers to be used in accordance with the invention is subject to the following definitions.

Alkyl radicals embrace straight-chain or branched, saturated carbon chains of 1 to 20 carbon atoms. The following radicals may be mentioned by way of example: alkyl radicals having 1 to 12 carbon atoms, such as the C$_1$–C$_6$ alkyl radicals methyl, ethyl, n-propyl, isopropyl, n-butyl, sec-butyl, isobutyl, t-butyl, n-pentyl, sec-pentyl, isopentyl, n-hexyl, 1-, 2- and 3-methylpentyl; and longer-chain radicals, such as unbranched heptyl, octyl, nonyl, decyl, undecyl, lauryl and the singly or multiply branched analogs thereof; and also alkyl radicals having more than 12 carbon atoms, such as unbranched tridecyl, myristyl, pentadecyl, palmityl, heptadecyl, stearyl, nonadecyl and eicosyl and also the singly or multiply branched analogs thereof.

Cycloalkyl radicals embrace in particular C$_3$–C$_{12}$ cycloalkyl radicals, such as cyclopropyl, cyclobutyl, cyclopentyl, cyclohexyl, cycloheptyl, cyclooctyl, cyclopropylmethyl, cyclopropylethyl, cyclopropylpropyl, cyclobutylmethyl, cyclobutylethyl, cyclopentylethyl, cyclopentylpropyl, cyclopentylbutyl, cyclopentylpentyl, cyclopentylhexyl, and the like.

Examples of preferred aralkyl radicals are phenyl and naphthyl, especially phenyl.

Examples of aralkyl radicals are aryl-C$_1$–C$_{10}$-alkyl and especially aryl-C$_1$–C$_6$-alkyl radicals, the aryl and alkyl moieties being as defined above.

The sum of all percentages (mol %, % by weight) for describing a composition is in each case 100.

Preferred substituents of the radicals R$^2$ and R$^3$ are —OH, —O—C$_1$–C$_6$-alkyl, —O-phenyl, —SH, —S—C$_1$–C$_6$-alkyl, —S—phenyl, —NH$_2$, —NH—C$_1$–C$_6$-alkyl, —NH-phenyl, —N(C$_1$–C$_6$-alkyl)$_2$, —N(C$_1$–C$_6$-alkyl)$_3$$^+$Z$^-$, —COOH, —COO—C$_1$–C$_6$-alkyl, —CONH$_2$, —CONH—C$_1$–C$_6$-alkyl, —CON(C$_1$–C$_6$-alkyl)$_2$, —CN and —SO$_3$H.

Preferred counterions Z$^-$ are Cl$^-$, Br$^-$, H$_2$PO$_4$$^-$, SO$_4$$^{2-}$, NO$_3$$^-$, HCOO$^-$, phenyl-SO$_3$$^-$.

One preferred embodiment of the invention uses polymers comprising
  a) from 0.1 to 100 mol % units of the above formulae I and/or II
  b) from 0 to 99.9 mol % of vinylamine units of the formula III

in which R$^1$ is as defined above,
  c) from 0 to 99.9 mol % of monoethylenically unsaturated monomer units other than a) and b), selected preferably from N-vinylcarboxamides such as N-vinyl-C$_1$–C$_6$-carboxamides, N-vinylpyrrolidone, N-vinylcaprolactam, N-vinylurea, N-vinylimidazoles, N-vinylimidazolines, vinyl alcohol, vinyl formate, vinyl acetate, vinylpropionate, vinyl butyrate, C$_1$–C$_6$ vinyl ethers, monoethylenically unsaturated C$_3$–C$_8$ carboxylic acids and dicarboxylic acids, and the esters, amides, anhydrides and nitriles thereof; and
  d) from 0 to 5 mol % of at least diethylenically unsaturated monomer units, preferably methylenebisacrylamide, glycol diacrylate, glycerol triacrylate, glycol dimethacrylate, glycerol trimethacrylate, divinylbenzene, divinyldioxane, pentaerythritol triallyl ether, pentaallylsucrose, divinylurea and divinylethyleneurea.

Particular preference is given to the use of polymers comprising a) from 1 to 100 mol %, in particular from about 5 to 100 mol %, of units of the formula I and/or II in which $R^1$ is H, $R^2$ and $R^3$ are selected independently of one another from H, $C_1$–$C_6$ alkyl and phenyl, and x is an integer from 1 to 10, b) from 0 to 99 mol %, in particular from about 0 to 95 mol %, of vinylamine units of the formula III, in which $R^1$ is H, and c) from 0 to 99 mol %, in particular from about 0 to 95 mol %, of at least one other ethylenically unsaturated monomer selected from N-vinylformamide, N-vinylpyrrolidone, N-vinylcaprolactam, N-vinylurea, vinyl alcohol, vinyl formate, vinyl acetate, vinyl propionate, $C_1$–$C_6$ vinyl ethers, acrylic acid, methacrylic acid and the esters, amides, anhydrides and nitriles thereof.

Special preference is given to the use of polymers comprising a) from 1 to 100 mol %, in particular from about 5 to 95 mol %, of units of the formula I and/or II in which $R^1$ is H, one of the radicals $R^2$ and $R^3$ is H and the other radical is H or methyl, and x is an integer from 1 to 6, and b) from 0 to 99 mol %, in particular from about 0 to 95 mol %, of vinylamine units, and c) from 0 to 99 mol %, in particular from about 0 to 95 mol %, of N-vinylformamide units.

The polymers to be used in accordance with the invention and comprising as essential structural elements units of the formula IV and/or V

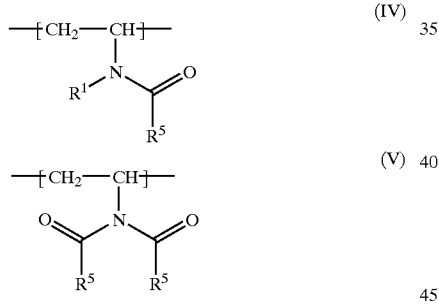

in which $R^1$ is alkyl, cycloalkyl, aryl or aralkyl and the radicals $R^5$ independently of one another are selected from alkyl, cycloalkyl, aryl and aralkyl, substituted one or more times if desired by OH, O-alkyl, O-aryl, SH, S-alkyl, S-aryl, $NH_2$, NH-alkyl, NH-aryl, N(alkyl)$_2$, in protonated form if desired, N(alkyl)$_3^+Z^-$, where Z is the radical of an organic or inorganic acid, COOH, COO-alkyl, $CONH_2$, CONH-alkyl, CON(alkyl)$_2$, CN or $SO_3H$; or are a radical of the formula VI

in which $R^2$, $R^3$ and x are as defined above and $R^2$ and $R^3$ can also independently of one another be OH, and the corresponding acid addition salts of these polymers are preferably prepared by reacting a prepolymer containing vinylamine units of the formula III

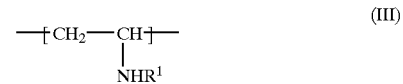

in which $R^1$ is as defined above with a compound of the formula VII

in which
$R^5$ is as defined above and
$R^6$ is alkyl, aralkyl or aryl, or
$R^5$ and $R^6$ together are a group of the formula VI

in which $R^2$, $R^3$ and x are as defined above, and converting the product, if desired, into the corresponding acid addition salt.

Use is made in particular of a prepolymer comprising b) from 0.1 to 100 mol % of vinylamine units of the formula III c) from 0 to 99.9 mol % of monoethylenically unsaturated monomer units other than a) and d) from 0 to 5 mol % of at least diethylenically unsaturated monomer units.

Components b), c) and d) are defined as indicated above.

Using the process described above it is therefore possible to prepare not only the novel polymers characterized by the hydroxylated N-vinylcarboxamide units of the formulae I and II but also all other polymers characterized by units of the formulae IV and V.

The polymers preferably prepared by this process characteristically contain units of the formulae I and/or II. They are prepared by reacting a prepolymer as defined above with lactones of the formula VIII

in which $R^2$ and $R^3$ independently of one another are H, OH or a $C_1$–$C_{20}$ alkyl, $C_3$–$C_{12}$ cycloalkyl, aryl or aralkyl radical which is unsubstituted or substituted by a functional group such as OH, O-alkyl, O-aryl, SH, S-alkyl, S-aryl, $NH_2$, NH-alkyl, NH-aryl, N(alkyl)$_2$ in the form of the free amine and/or in protonated form, N(alkyl)$_3^+Z^-$, COOH, COO-alkyl, CONH$_2$, CONH-alkyl, CON(alkyl)$_2$ CN or SO$_3$H; and x is an integer from 1 to 20.

Examples of suitable such lactones are acetolactone (x=1), 2-methylacetolactone, 2,2-dimethylacetolactone, 2,2-diphenylacetolactone, 2-ethylacetolactone, 2,2-diethylacetolactone, 2-benzylacetolactone, β-propiolactone (x=2), 2-methyl-β-propiolactone, 3-methyl-β-propiolactone, 2,3-dimethyl-β-propiolactone, 3,3-dimethyl-β-propiolactone, 3-phenyl-β-propiolactone, 3-ethyl-β-propiolactone, 3-benzyl-β-propiolactone, γ-butyrolactone (x=3), 4-methyl-γ-butyrolactone, 3-methyl-γ-butyrolactone, 4-ethyl-γ-butyrolactone, 3,3-dimethyl-γ-butyrolactone, 4-phenyl-γ-butyrolactone, 4-benzyl-γ-butyrolactone, δ-valerolactone (x=4), γ-valerolactone, 2-methyl-δ-valerolactone, 5-phenyl-δ-valerolactone, 5-benzyl-δ-valerolactone, 2-ethyl-δ-valerolactone, 3-hydroxy-3-methyl-δ-valerolactone, ε-caprolactone (x=5) and also exaltolide (x=18) or else hydroxy-substituted lactones such as lactolactone or mandelolactone. Preference is given to the use of β-propiolactone, γ-butyrolactone, γ-valerolactone, δ-valerolactone and ε-caprolactone.

Also suitable are lactones of aldonic acids, such as glyceric acid, threonic acid, erythronic acid, ribonic acid, arabinonic acid, xylonic acid, lyxonic acid, allonic acid, atronic acid, gluconic acid, mannonic acid, gulonic acid, idonic acid, galactonic acid and talonic acid, or aldonic acid lactones of di- and oligosaccharides such as maltose or cellobiose.

In a second variant of the process, a prepolymer as defined above is reacted with carboxylic esters of the formula (VII)

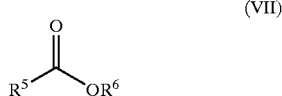

(VII)

in which
R$^5$ is a C$_1$–C$_{20}$-alkyl, C$_3$–C$_{12}$-cycloalkyl, aryl or aralkyl radical which is unsubstituted or substituted by a functional group selected from OH, O-alkyl, O-aryl, SH, S-alkyl, S-aryl, NH$_2$, NH-alkyl, NH-aryl, N(alkyl)$_2$ in the form of the free amine and/or in protonated form, N(alkyl)$_3$$^+$Z$^-$, COOH, COO-alkyl, CONH$_2$, CONH-alkyl, CON(alkyl)$_2$, CN and SO$_3$H; and R$^6$ is C$_1$–C$_6$-alkyl, aralkyl or aryl.

In this process variant it is preferred to use prepolymers comprising as copolymerized units
a) from 5 to 100 mol % of primary vinylamine, and
b) from 0 to 95 mol % of other ethylenically unsaturated monomers from the group consisting of N-vinylformamide, N-vinylpyrrolidone, N-vinylcaprolactam, N-vinylurea, vinyl alcohol, vinyl formate, vinyl acetate, vinyl propionate, acrylic acid and/or acrylonitrile.

Possible examples of suitable esters of the formula VII are methyl, ethyl, propyl, isopropyl, benzyl, phenyl, n-butyl, n-pentyl and n-hexyl esters of aliphatic and aromatic monocarboxylic acids such as, for example, acetic acid, propionic acid, butyric acid, isobutyric acid, n-valeric acid, pivalic acid, caproic acid, cyclopentylcarboxylic acid, cyclohexyl- carboxylic acid, enanthic acid, caprylic acid, nonanoic acid, capric acid, lauric acid, myristic acid, palmitic acid, stearic acid, benzoic acid, 1-naphthalenecarboxylic acid, 2-naphthalenecarboxylic acid, phenylacetic acid and β-phenylpropionic acid or dicarboxylic acids such as, for example, oxalic acid, malonic acid, succinic acid, glutaric acid, adipic acid, pimelic acid and suberic acid. These carboxylic acids can if desired also be substituted by functional groups, such as OH, O-alkyl, O-aryl, halogen, SH, S-alkyl, S-aryl, NH$_2$, NH-alkyl, NH-aryl, N(alkyl)$_2$ in the form of the free amine and/or in protonated form, N(alkyl)$_3$$^+$Z$^-$, COOH, COO-alkyl, CONH$_2$, CONH-alkyl, CON(alkyl)$_2$, CN, SO$_3$H. Examples of substituted carboxylic acids are chloroacetic acid, bromoacetic acid, cyanoacetic acid, α-chloropropionic acid, β-chloropropionic acid, α-bromopropionic acid, β-bromopropionic acid, glycolic acid, lactic acid, malic acid, tartaric acid, mandelic acid, salicylic acid, mercaptoacetic acid, α-mercaptopropionic acid, β-mercaptopropionic acid, glycine, N-methylglycine, N,N-dimethylglycine, choline, α-alanine, β-alanine, valine, leucine, isoleucine, serine, threonine, lysine, phenylalanine, thyrosine and proline. Also suitable are esters of polyhydric alcohols, such as glycol or polyglycols, glycerol, mannitol, sorbitol, glucose, it being possible for one or more hydroxyl groups to be esterified with carboxylic acids. Preference is given to the use of acetic, propionic, butyric, benzoic, lauric, palmitic and stearic methyl esters or triglycerides of higher fatty acids such as lauric acid, palmitic acid and stearic acid.

Reactions of carboxylic esters and lactones with amines are widely described in the literature. Since the abovementioned prepolymers containing vinylamine units in copolymerized form are predominantly soluble in water, it is judicious to conduct the reaction with the esters or lactones of the formula VII or VIII respectively in the presence of water. For instance, the reaction can be carried out either in aqueous solution or in mixtures of water with other inert solvents. Examples of suitable solvents are those in which the esters and lactones are soluble, such as methanol, ethanol, isopropanol, n-propanol, n-butanol, sec-butanol, tert-butanol, glycol, dimethylethylene glycol, tetrahydrofuran, dioxane, hexamethylphosphoramide, acetonitrile or acetone, and also mixtures of said solvents. The reaction preferably takes place in aqueous solution at a pH of from 7 to 12, preferably from 9 to 11. It is also possible to conduct the reaction in buffered solution, in which case the buffer system comprising primary/secondary phosphate is particularly suitable. The concentration of the polymer in the aqueous solution, depending on molecular weight, is from 5 to 60% by weight, preferably from 10 to 30% by weight, so that the solution is readily stirrable during the reaction.

The reaction temperature is from 20 to 200° C., preferably from 40 to 120° C., and with particular preference, from 50 to 100° C. If the reaction is carried out at temperatures above the boiling point of the ester or lactone or above the boiling temperature of the inert solvent, it is conducted under pressure in a corresponding pressure vessel. The reaction time is from 1 to 20 hours, preferably from 3 to 10 hours. The alcohols which are liberated in the course of the reaction of the amine functions with esters can be removed if desired by distillation during the reaction and so be withdrawn from the equilibrium.

Depending on the desired degree of amidation in the end product, from 1 to 5, preferably from 1 to 2.5 equivalents of ester or lactone are added per vinylamine unit to be converted. Secondary vinylamine units (R$^1$≠H) react exclusively to give structures of the formula I. In the case of primary amine functions, both structures I and structures II are formed depending on the amount of lactone used. If a substoichiometric amount of the lactone is used, then the formation of structure I is preferred.

The formation of amide reduces the number of basic groups and thus the cationic charge density of the polymer, and this can be detected by polyelectrolyte titration. In terms of the lactone used, the conversion is generally more than 50%, in the majority of cases more than 70%. When reaction is complete, the solution can be adjusted to the desired pH by adding acids or bases. Another possibility, however, is to isolate the polymer by precipitation in alcohols or acetone or to free the solution from low molecular mass constituents by dialysis. The composition can be determined by means of elemental analysis and also by $^1$H NMR and IR spectroscopy.

The resulting polymers have molecular weights in particular of from 1000 to 10 million, preferably from 10,000 to 5 million, corresponding to K values of from about 5 to 300 and from 10 to 250, respectively, as measured on 1% strength aqueous solutions at a pH of 7 and at 25° C. in accordance with H. Fikentscher, Cellulose-Chemie 13 (1932) 58 to 64 and 71 to 74.

In order to obtain a substantially colour-stable polymer solution in the course of storage, reaction with the esters or lactones is followed if desired by the addition of antioxidants, reducing agents or aldehyde scavengers. Examples of antioxidants, which usually act as free-radical scavengers or UV stabilizers, are secondary aromatic amines, phenol, alkylphenols, thioethers, phosphites or mixtures of compounds from said classes of substance. Examples of suitable secondary aromatic amines are 4,4'-bis(phenylmethyl)diphenylamine, 4,4'-bis(tert-butyl) diphenylamine or mixtures thereof. Examples of alkylphenols which are suitable as antioxidants are 2,6-dimethyl-4-tert-butylphenol, 2,4,6-trimethylphenol, 2,4-di-tert-butyl-6-methylphenol or mixtures thereof. Suitable thioethers are dialkyl 3,3'-thiodipropionate, poly-2,3-dimethylphenyl 1,4-disulfide, dibenzyl sulfide and dialkyl disulfides such as, for example, dioctadecyl disulfide. Phosphites suitable as antioxidants are, for example, trisnonylphenyl phosphite, di(2, 4-di-tert-butyl-phenyl)pentaerythritol diphosphite and diphenylenedecyl phosphite.

Examples of suitable reducing agents are sodium borohydride, sodium cyanoborohydride, dithionites, such as sodium, potassium or zinc dithionite, or else hypophosphorous acid.

Examples of aldehyde scavengers are compounds containing NH groups, such as urea, ethyleneurea, melamine, guanidine, phenylguanidine or mixtures of said compounds. Also notable are alkali metal bisulfites such as sodium or potassium bisulfite.

Antioxidants, reducing agents and aldehyde scavengers are used respectively in amounts from 0.01 to 20% by weight, preferably from 0.1 to 16% by weight, based on the polymers.

The prepolymers required as starting material for conducting the preferred process are obtained in accordance with known methods: for example, by free-radically initiated homo- and copolymerization of N-vinylcarboxamides of the formula IX

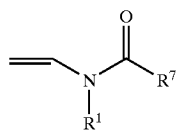

(IX)

in which $R^1$ is as defined above and $R^7$ is H or $C_1$–$C_6$ alkyl followed by partial or complete hydrolytic elimination of the group

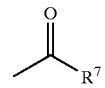

preferably with the aid of acids, bases or enzymes.

The hydrolysis is preferably conducted in water under the action of acids, bases or enzymes, but can also take place in the absence of said hydrolysis agents. Depending on the reaction conditions during the hydrolysis, i.e. the amount of acid or base, based on the polymer to be hydrolyzed, and on the reaction time and reaction temperature, the resulting degree of hydrolysis varies. The hydrolysis is carried out such that from 0.1 to 100 mol %, preferably from 1 to 99 mol % and, with very particular preference, from 5 to 95 mol % of the carboxylic acid radicals are hydrolytically eliminated.

Examples of acids suitable for the hydrolysis are mineral acids, such as hydrogen halide (gaseous or in aqueous solution), sulfuric acid, nitric acid, phosphoric acid (ortho-, meta- or polyphosphoric acid) or organic acids, examples being $C_1$–$C_5$ carboxylic acids, such as formic acid, acetic acid or propionic acid, or aliphatic and aromatic sulfonic acids, such as methanesulfonic acid, benzenesulfonic acid or toluenesulfonic acid. In the case of hydrolysis with acids the pH is from 0 to 5. For each carboxylic acid radical in the polymer that is to be eliminated, from 0.05 to 1.5 equivalents of acid are required, preferably from 0.4 to 1.2 equivalents.

In the case of hydrolysis with bases it is possible to use metal hydroxides of metals from the first and second main groups of the Periodic Table, examples being lithium hydroxide, sodium hydroxide, potassium hydroxide, calcium hydroxide, strontium hydroxide and barium hydroxide. Also suitable, however, are ammonia or alkyl derivatives of ammonia, e.g. alkylamines or arylamines such as triethylamine, monoethanolamine, diethanolamine, triethanolamine, morpholine, piperidine, pyrrolidine or aniline. In the case of hydrolysis with bases the pH is from 8 to 14. The bases can be used in solid, liquid or else possibly gaseous state, in diluted or undiluted form. Preference is given to the use of ammonia, sodium hydroxide solution or potassium hydroxide solution. Hydrolysis in the acidic or alkaline pH range takes place at temperatures from 20 to 170° C., preferably from 20 to 120° C. It is over after about 2 to 8, preferably 3 to 5 hours.

A procedure which has proven particularly appropriate is that in which the acids or bases are added in aqueous solution. Following the hydrolysis, a neutralization is generally carried out so that the pH of the hydrolyzed polymer solution is from 3 to 12, preferably from 8 to 11. Neutralization is necessary when continuation of the hydrolysis of partly hydrolyzed polymers is to be avoided or delayed.

The hydrolysis can also be performed with the aid of enzymes, such as amidases or proteases, for example.

In the course of the hydrolysis, further modification of the polymers may take place to the effect that the copolymerized comonomers are likewise hydrolyzed. From copolymerized units of vinyl esters, for example, vinyl alcohol units are formed.

Depending on the hydrolysis conditions, the copolymerized vinyl esters may undergo complete or partial saponification.

In the case of partial hydrolysis of copolymers containing vinyl acetate units, the hydrolyzed copolymer contains not only unaltered vinyl acetate units but also vinyl alcohol units, and also N-vinylcarboxamide and vinylamine units. Units of monoethylenically unsaturated carboxylic anhydrides, carboxylic esters and carboxamides may give rise in the case of hydrolysis to carboxylic acid units. Copolymerized monoethylenically unsaturated carboxylic acids themselves are not altered during the hydrolysis. It is possible for carboxamide and carboxylic acid units to be formed from copolymerized monoethylenically unsaturated nitriles too. The degree of hydrolysis of the copolymerized comonomers can easily be determined by analysis.

The prepolymers obtained following hydrolytic cleavage have molecular weights of from 1000 to 10 million, preferably from 10,000 to 5 million, corresponding to K values of from about 5 to 300 and from 10 to 250, respectively, as measured on 1% strength aqueous solutions at a pH of 7 and at 25° C. in accordance with H. Fikentscher, Cellulose-Chemie 13 (1932) 58 to 64 and 71 to 74.

Preference is given to prepolymers comprising units of
a) from 1 to 100 mol % of primary vinylamine, and
b) from 0 to 99 mol % of other ethylenically unsaturated monomers from the group consisting of N-vinylformamide, N-vinylpyrrolidone, N-vinylcaprolactam, N-vinylurea, vinyl alcohol, vinyl formate, vinyl acetate, vinyl propionate, acrylic acid and acrylonitrile.

Particularly suitable prepolymers are those, for example, which consist exclusively of vinylamine units of the above formula III in which $R^1$ is H, $C_1$–$C_{12}$ alkyl, $C_3$–$C_{12}$ cycloalkyl, aryl or aralkyl and in which the radicals $R^1$ can be either identical or different. It is preferred to start from polymers containing primary vinylamine units ($R^1$=H).

Further suitable prepolymers are copolymers which in addition to the vinylamine units contain up to 99.9 mol %, preferably up to 95 mol %, of other units of ethylenically unsaturated monomers. Examples that may be mentioned include N-vinylformamide, N-vinyl-N-methylformamide, N-vinyl-N-ethylformamide, N-vinylpropylformamide, N-vinyl-N-isopropylformamide, N-vinyl-N-butylformamide, N-vinyl-N-sec-butylformamide, N-vinyl-N-tert-butylformamide, N-vinyl-N-pentylformamide, vinyl alcohol and also vinyl esters of saturated carboxylic acids having 1 to 6 carbon atoms, such as vinyl formate, vinyl acetate, vinyl propionate and vinyl butyrate. Also suitable are copolymers containing unsaturated $C_3$–$C_8$ carboxylic acids, such as acrylic acid, methacrylic acid, maleic acid, crotonic acid, itaconic acid and vinylacetic acid, and also the alkali metal and alkaline earth metal salts, esters, amides and nitriles thereof, examples being methyl acrylate, methyl methacrylate, ethyl acrylate, ethyl methacrylate, propyl acrylate and butyl acrylate, or containing glycol and/or polyglycol esters of ethylenically unsaturated carboxylic acids, with only one OH group of the glycols and polyglycols being esterified in each case, examples being hydroxyethyl acrylate, hydroxyethyl methacrylate, hydroxypropyl acrylate, hydroxypropyl methacrylate, hydroxybutyl acrylate and hydroxybutyl methacrylate, or else containing acrylic and methacrylic monoesters of polyalkylene glycols with a molecular weight of from 1500 to 10,000.

Further suitable prepolymers are copolymers containing esters of ethylenically unsaturated carboxylic acids with amino alcohols, such as, for example, dimethylaminoethyl acrylate, dimethylaminoethyl methacrylate, diethylaminoethyl acrylate, diethylaminoethyl methacrylate, dimethylaminopropyl acrylate, dimethylaminopropyl methacrylate, diethylaminopropyl acrylate, diethylaminopropyl methacrylate, dimethylaminobutyl acrylate and diethylaminobutyl acrylate. The basic acrylates are in the form of the free bases, of the salts with mineral acids such as hydrochloric acid, sulfuric acid and nitric acid, for example, the salts of organic acids, such as formic acid or benzenesulfonic acid, or in quaternized form.

Examples of suitable quaternizing agents are dimethyl sulfate, diethyl sulfate, methyl chloride, ethyl chloride and benzyl chloride.

Further suitable prepolymers are copolymers containing units of unsaturated amides, such as acrylamide, methacrylamide and also N-alkylmono- and -diamides with alkyl radicals of 1 to 6 carbon atoms, examples being N-methylacrylamide, N,N-dimethylacrylamide, N-methylmethacrylamide, N-ethylacrylamide, N-propylacrylamide and tert-butylacrylamide, and also basic (meth)acrylamides, such as dimethylaminoethylacrylamide, dimethylaminoethylmethacrylamide, diethylaminoethylacrylamide, diethylaminoethylmethacrylamide, dimethylaminopropylacrylamide, dimethylaminopropylmethacrylamide, diethylaminopropylacrylamide and diethylaminopropylmethacrylamide, in copolymerized form.

It is also possible as prepolymers to use copolymers containing units of $C_1$–$C_6$ vinyl ethers, examples being vinyl methyl ether, vinyl ethyl ether, vinyl propyl ether, vinyl isopropyl ether, vinyl butyl ether, vinyl isobutyl ether, vinyl pentyl ether and vinyl hexyl ether.

Further suitable prepolymers are copolymers containing units of N-vinylpyrrolidone, N-vinylcaprolactam, N-vinylurea and substituted N-vinylureas, such as N-vinyl-N'-methylurea, N-vinyl-N'-dimethylurea and N-vinylimidazole and substituted N-vinylimidazoles, such as N-vinyl-2-methylimidazole, N-vinyl-4-methylimidazole, N-vinyl-5-methylimidazole, N-vinyl-2-ethylimidazole and N-vinylimidazolines such as N-vinylimidazoline, N-vinyl-2-methylimidazoline and N-vinyl-2-ethylimidazoline, for example.

In this case the imidazole and imidazoline functions are in the form of the free bases or else in neutralized form with mineral acids or organic acids, or else in quaternized form, the quaternization preferably being conducted with dimethyl sulfate, diethyl sulfate, methyl chloride or benzyl chloride.

Finally, it is also possible as prepolymers to use copolymers containing monomer units having sulfo groups, such as, for example, vinylsulfonic acid, allylsulfonic acid, methallylsulfonic acid, styrenesulfonic acid or 3-sulfopropyl acrylate, 3-sulfopropyl methacrylate and 2-acrylamido-2-methylpropanesulfonic acid. The compounds containing acid groups can be used in the form of the free acids or of the ammonium, alkali metal or alkaline earth metal salts.

The prepolymers can be modified further by copolymerizing from 0 to 5 mol % of units of monomers having at least two nonconjugated ethylenically unsaturated double bonds. Such comonomers are usually used in copolymerizations as crosslinkers. The use of these comonomers during the copolymerization brings about an increase in the molecular masses of the copolymers. Examples of suitable compounds of this type are methylenebisacrylamide, esters of acrylic acid and methacrylic acid with polyhydric alcohols, such as glycol diacrylate, glycerol triacrylate, glycol dimethacrylate and glycerol trimethacrylate, and also polyols, such as pentaerythritol and glucose, which are esterified at least twice with acrylic or methacrylic acid. Further suitable crosslinkers are divinylbenzene, divinyldioxane, pentaerythritol triallyl ether, pentaallylsucrose, divinylurea and divinylethyleneurea.

The (co)polymerization for preparing the prepolymers can be conducted in the presence or else in the absence of an inert solvent or diluent. Since polymerization in the absence of inert solvents or diluents usually leads to nonuniform polymers, it is preferred to carry out polymerization in an inert solvent or diluent. Examples of suitable inert solvents are those in which the open-chain N-vinylcarboxamides are soluble. For solution polymerization, examples of suitable solvents are inert solvents such as methanol, ethanol, isopropanol, n-propanol, n-butanol, tetrahydrofuran, dioxane and water and also mixtures of said inert solvents. The polymerization can be conducted continuously or batchwise. It takes place in the presence of free-radical initiators, which are used in amounts of from 0.01 to 20% by weight, preferably from 0.05 to 10% by weight, based on the monomers. If desired, the polymerization can also be initiated solely by the action of high-energy radiation, examples being electron beams or UV rays.

In order to prepare polymers having low molecular weights of, for example, from 1000 to 100,000, preferably from 5000 to 50,000, the polymerization is judiciously conducted in the presence of regulators. Examples of suitable regulators are organic compounds containing sulfur in bonded form. They include mercapto compounds, such as mercaptoethanol, mercaptopropanol, mercaptobutanol, mercaptoacetic acid, mercaptopropionic acid, butyl mercaptan and dodecyl mercaptan. Further suitable regulators are allyl compounds, such as allyl alcohol, aldehydes such as formaldehyde, acetaldehyde, propionaldehyde, n-butyraldehyde and isobutyraldehyde, formic acid, ammonium formate, propionic acid, hydrazine sulfate, and butenols.

If the polymerization is carried out in the presence of regulators, the amount of the latter required is from 0.05 to 20% by weight, based on the monomers used in the polymerization.

The polymerization of the monomers usually takes place under an inert gas atmosphere in the absence of atmospheric oxygen. During the polymerization, it is common to provide for thorough mixing of the reactants. In the case of relatively small batches, where safe dissipation of the heat of polymerization is ensured, the monomers can be polymerized batchwise by heating the reaction mixture to the polymerization temperature and then allowing the reaction to proceed. These temperatures lie within the range from to 180° C., it being possible to operate under atmospheric pressure or under subatmospheric or else superatmospheric pressure. Polymers of high molecular weight are obtained when the polymerization is conducted in water. For the preparation of water-soluble polymers, this can take place, for example, in aqueous solution, as a water-in-oil emulsion, or by the technique of inverted suspension polymerization.

In order to prevent saponification of the monomeric N-vinylcarboxamides during polymerization in aqueous solution, the polymerization is conducted preferably within a pH range of 4 to 9, in particular from 5 to 8. In many cases it is additionally advisable to work in the presence of buffers, an example being primary or secondary sodium phosphate.

The abovementioned polymers have a strong microbicidal action and can therefore be used to control unwanted microorganisms. The active substances and the formulations preparable therefrom are intended chemically to destroy, deter, render harmless or prevent damage by harmful organisms or to control them in some other way.

The polymers to be used in accordance with the invention and the formulations thereof prevent the microbial infestation of industrial materials and so can be used for in-can preservation. They are also used for the biocidal finishing of products: that is, they can be used for film preservation.

By industrial materials are meant nonliving materials as obtained in industrial processes. Examples of industrial materials to be protected by the use according to the invention of the polymers and formulations against microbial alteration or destruction are as follows:

Finishes, drilling oils, dispersions, adhesives, glues, pigment formulations, paper, textiles, textile assistants, leather, leather assistants, wood, coatings, antifouling paints, plastics articles, cosmetics, detergents, cleaning products, cooling lubricants, hydraulic fluids, joint-sealing compounds, putties, thickener solutions and other materials which may be infested or broken down by microorganisms.

The polymers and formulations can also be used in water treatment. By water treatment is meant the addition of the polymers and formulations to process water: for example, for slime control in the paper industry or for the control of harmful organisms in the sugar industry. They prevent or control the growth of microorganisms in cooling circuits, air humidifiers, or in drilling and conveying fluids in the petroleum industry.

The polymers and their formulations can also be used for disinfection.

Examples that may be mentioned of microorganisms which can bring about the breakdown of or a change in industrial materials are bacteria, viruses, spores, yeasts, fungi, algae and slime organisms. The polymers to be used in accordance with the invention and their formulations are preferably active against bacteria, yeasts and fungi.

The following microorganisms may be mentioned by way of example:

Staphylococcus aureus
Escherichia coli
Proteus mirabilis
Citrobacter freudii
Pseudomonas aeruginosa
Candida albicans
Saccharomyces cerevisiae
Alternaria alternata
Aspergillus niger
Penicillium funiculosum Depending on their chemical and physical properties, the polymers to be used in accordance with the invention can be converted into customary formulations and preparations, such as emulsions, suspensions, dispersions, solutions, powders and pastes, for example, or in combination with carrier materials. For this purpose, surface-active substances (e.g., anionic surfactants such as alkylsulfonates, ether sulfates; nonionic surfactants such as fatty alcohol ethoxylates, fatty alcohol ester ethoxylates, sorbitan esters, polyalkylene glycols; amphoteric surfactants), complexing agents (e.g., ethylenediaminetetraacetic acid, nitrilotriacetic acid, methylglycinetriacetic acid), solubilizers (e.g., alcohols such as ethanol, n-propanol, isopropanol or glycols, such as propylene glycol and polypropylene glycol), acids or bases (e.g., phosphoric acid, sodium hydroxide solution), inorganic salts and/or further additives (such as corrosion inhibitors, foam suppressants, guide substances, dyes) are added to the formulations and preparations if desired.

Processes for preparing such biocidally active formulations are known to the skilled worker and are described in the relevant literature.

The activity and the spectrum of action of the polymers to be used in accordance with the invention and, respectively, of the compositions or formulations preparable therefrom can be raised by adding, if desired, further microbicidally active compounds such as fungicides, bactericides and/or herbicides, insecticides and/or other active substances for the purpose of broadening the spectrum of action or for obtaining particular effects. In many cases, synergistic effects are obtained in this case: that is, the spectrum of action of the mixture exceeds the action of the individual components. Such substances are known per se to the skilled worker and are described in the literature.

Particularly preferred co-components are 5-aminoisothiazoles of the formula X

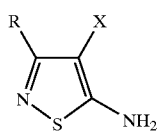

in which

R is hydrogen or $C_1$–$C_4$ alkyl and

X is halogen, $NO_2$, CN or SCN.

Preferred compounds are those in which R is $C_1$–$C_4$ alkyl, especially methyl.

Further preferred compounds are those in which x is CN and especially SCN.

In a particularly preferred embodiment use is made of 3-methyl-4-thiocyanato-5-aminoisothazole (formula Xc)

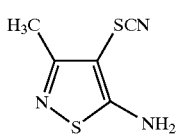

and its metal complexes and acid addition salts.

The abovementioned aminoisothiazoles X are obtained using a reaction sequence which is known per se from EP-A-640 597 and in which isothiazoles of the formula XI

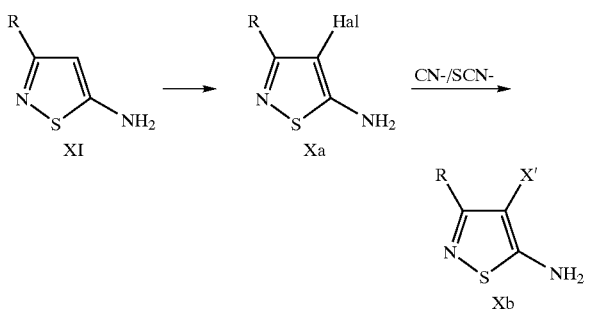

are converted using a halogenating agent into the halogen compounds Xa, in which Hal is F, Cl, Br or I, which if required are then transformed by reaction with thiocyanates or cyanides into the compounds Xb, where X' is SCN or CN. The preparation of isothiazoles of the formula XI is described, for example, in DE-A 17 70 819. The preparation of 3-methyl-5-aminoisothiazole was described by A. Adams et al. in J. Chem. Soc. 1959, 3061.

The microbicidal compositions or concentrates used to protect industrial materials contain the polymers to be used in accordance with the invention, or the active-substance combinations, in a concentration of from 0.005 to 70% by weight, in particular from 0.05 to 40% by weight, based on the overall weight.

The concentrations in which the polymers to be used are employed is guided by the nature and the incidence of the microorganisms to be controlled and by the composition of the material to be protected.

Microbicidal and microbistatic properties are determined experimentally. Highly suitable test methods have been described in detail by the German Society of Hygiene and microbiology (DGHM) for the testing of disinfectants.

The results in the Use Examples below were determined as follows:

Tube dilution tests were carried out to determine the minimum inhibitory concentration MIC in accordance with the "Guidelines for the Testing and Evaluation of Chemical Disinfection Procedures (status 1.1.81, procedure slightly modified)" using casein peptone-soybean flour peptone medium. Dilution was made with water of standardized hardness without further auxiliaries such as, for example, surfactants. The adjustment of the pH to 7.2±0.2 was carried out with 0.1 mol/l NaOH or 0.1 mol/l HCl. The gradation of the test concentrations was in accordance with the concentration stages proposed by the DGHM. Evaluation was made after incubation at 36° C. for 72 hours.

The table below indicates the strain numbers of the microorganisms:

| Test microorganisms: | |
| --- | --- |
| Staphylococcus aureus | ATTC 6538 |
| Escherichia coli | ATTC 11229 |
| Proteus mirabilis | ATTC 14153 |
| Pseudomonas aeruginosa | ATTC 15442 |
| Candida albicans | ATTC 10231 |

The K values of the polymers were determined in accordance with H. Fikentscher, Cellulose-Chemie, 13 (1932) 58 to 64 and 71 to 74 in 5% strength by weight aqueous sodium chloride solution at 25° C. and a pH of 7 with a polymer concentration of 0.5% by weight.

EXAMPLES

Examples 1 and 2 below describe the preparation of polymers to be used in accordance with the invention.

Example 1

A stirred apparatus with reflux condenser, thermometer and dropping funnel was charged with 500 g of an aqueous solution of a copolymer of 70 mol % polyvinylamine and 30 mol % N-vinylformamide, polymer content 7.7% by weight (≅524 mmol of vinylamine units), pH 10, K value 88. 13.5 g (≅156.8 mmol) of butyrolactone were added dropwise over the course of 10 minutes with vigorous stirring. The reaction mixture was subsequently heated at 70° C. for 5 hours. After cooling to room temperature, the solution was adjusted to a pH of 5 with 14 g of concentrated hydrochloric acid. This gave 527.5 g of copolymer solution having a viscosity of 13,250 mPas (Brookfield, 20° C.). The resulting polymer was composed of 56 mol % vinylamine units, 30 mol % N-vinylformamide units and 14 mol % N-vinyl-γ-hydroxybutyramide units. Accordingly, 67.3% of the butyrolactone used was reacted. The polymer content was 9.0% by weight.

Example 2

A stirred apparatus with reflux condenser, thermometer and dropping funnel was charged with 500 g of an aqueous solution of polyvinylamine, polymer content 22.6% by weight (≅2616 mmol of vinylamine units), pH 9, K value 30 ($M_w$≅10–20,000). 89.4 g (≅783 mmol) of caprolactone were added dropwise over the course of 20 minutes with vigorous stirring. The reaction mixture was subsequently heated at 80° C. for 5 hours. This gave 589.4 g of copolymer solution. The resulting polymer was composed of 73.5 mol % vinylamine units and 26.5 mol % N-vinyl-6-hydroxycaprbamide units. Accordingly, 88.4% of the caprolactone used was reacted. The polymer content was 32.5% by weight.

The table below indicates the minimum effective concentration (MIC), the concentrations being based on the respective polymer content.

TABLE 1

| Test microorganism | Polymer from Ex. 1 | Polymer from Ex. 2 |
|---|---|---|
| *Staphylococcus aureus* | 200 | 400 |
| *Escherichia coli* | 400 | 1200 |
| *Proteus mirabilis* | 3000 | 3000 |
| *Pseudomonas aeruginosa* | 3000 | 2000 |
| *Candida albicans* | 2000 | 4000 |

The results show the good microbicidal action of the polymers to be used in accordance with the invention.

We claim:

1. A method of controlling unwanted microorganisms which comprises treating the microorganisms or a material which is to be protected against damage caused by infestation of the microorganisms with an effective amount of a polymer comprising as essential structural elements units of the formula I and/or II

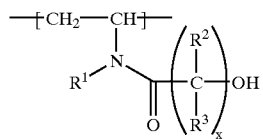
(I)

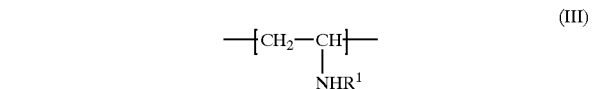
(II)

in which
   $R^1$ is H, alkyl, cycloalkyl, aryl or aralkyl,
   $R^2$ and $R^3$ independently of one another are defined as for $R^1$ or are selected from substituted alkyl, substituted cycloalkyl, substituted aryl or substituted aralkyl, the substituents being selected from OH, O-alkyl, O-aryl, SH, S-alkyl, S-aryl, $NH_2$, NH-alkyl, NH-aryl, $N(alkyl)_2$, in protonated form if desired, $N(alkyl)_3^+Z^-$, where Z is the radical of an organic or inorganic acid, COOH, COO-alkyl, $CONH_2$, CONH-alkyl, CON$(alkyl)_2$, CN and $SO_3H$; and
   the indices x in each case independently of one another are an integer from 1 to 20,
and their corresponding acid addition salts as biocides.

2. The method of claim 1, wherein the polymer has a weight-average molecular weight of from about $10^3$ to about $10^8$.

3. The method of claim 1, wherein the polymer comprises
   a) from 0.1 to 100 mol % units of the above formulae I and/or II
   b) from 0 to 99.9 mol % of vinylamine units of the formula III

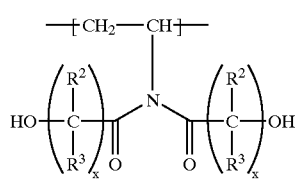
(III)

in which $R^1$ is as defined above,
   c) from 0 to 99.9 mol % of monoethylenically unsaturated monomer units (a) and (b), and
   d) from 0 to 5 mol % of units of monomers with at least two ethylenically unsaturated double bonds.

4. The method of claim 3, wherein the polymer has a weight-average molecular weight of from about $10^3$ to about $10^8$.

* * * * *